(12) United States Patent
Campos Beceiro

(10) Patent No.: US 9,447,247 B2
(45) Date of Patent: Sep. 20, 2016

(54) COMPOSITION AND PROCEDURE FOR OBTAINING A FILM OF MICRO POROUS THERMOPLASTIC POLYMER THAT IS ESPECIALLY SUITED TO THE PRODUCTION OF PERSONAL HYGIENE ARTICLES SUCH AS DIAPERS AND SANITARY TOWELS

(71) Applicant: KLONER, S.L., Sant Andreu de Llavaneras (ES)

(72) Inventor: Alberto Campos Beceiro, Sant Andreu de Llavaneres (ES)

(*) Notice: Subject to any disclaimer, the term of this patent is extended or adjusted under 35 U.S.C. 154(b) by 0 days.

(21) Appl. No.: 14/364,332

(22) PCT Filed: Jan. 10, 2013

(86) PCT No.: PCT/ES2013/070003
§ 371 (c)(1),
(2) Date: Jun. 11, 2014

(87) PCT Pub. No.: WO2013/104815
PCT Pub. Date: Jul. 18, 2013

(65) Prior Publication Data
US 2014/0329077 A1    Nov. 6, 2014

(30) Foreign Application Priority Data

Jan. 14, 2012    (ES) .................................. 201230055

(51) Int. Cl.
| | | |
|---|---|---|
| C08J 5/18 | (2006.01) |
| B32B 27/20 | (2006.01) |
| A61L 15/18 | (2006.01) |
| A61L 15/20 | (2006.01) |
| A61L 15/22 | (2006.01) |
| A61L 15/42 | (2006.01) |
| B29C 47/00 | (2006.01) |
| B32B 7/12 | (2006.01) |
| B32B 27/08 | (2006.01) |
| B32B 27/32 | (2006.01) |
| C08L 23/08 | (2006.01) |
| B29K 23/00 | (2006.01) |

(52) U.S. Cl.
CPC ...... *C08J 5/18* (2013.01); *A61L 15/18* (2013.01); *A61L 15/20* (2013.01); *A61L 15/225* (2013.01); *A61L 15/425* (2013.01); *B29C 47/0007* (2013.01); *B32B 7/12* (2013.01); *B32B 27/08* (2013.01); *B32B 27/20* (2013.01); *B32B 27/205* (2013.01); *B32B 27/32* (2013.01); *C08L 23/0815* (2013.01); *B29K 2023/0633* (2013.01); *B32B 2264/104* (2013.01); *B32B 2555/00* (2013.01); *B32B 2555/02* (2013.01); *C08J 2323/06* (2013.01); *C08J 2451/06* (2013.01); *Y10T 428/249978* (2015.04)

(58) Field of Classification Search
CPC .... C08J 5/18; C08J 2323/06; C08J 2451/06; B32B 27/20; B32B 27/32; C08K 3/26; C08K 9/04; Y10T 428/249978; Y10T 428/249986
See application file for complete search history.

(56) References Cited

U.S. PATENT DOCUMENTS

| | | | |
|---|---|---|---|
| 6,258,308 B1* | 7/2001 | Brady et al. ............... | 264/210.2 |
| 2004/0087235 A1* | 5/2004 | Morman ............ | A61F 13/4902 442/394 |
| 2004/0097616 A1* | 5/2004 | Hoppler ................... | C08K 9/06 523/216 |

*Primary Examiner* — Hai Vo
(74) *Attorney, Agent, or Firm* — Dowell & Dowell, PC

(57) ABSTRACT

The present invention consists in a method and a composition for obtaining films of a thermoplastic polymer, preferably polyethylene, that are non-breathable and heavily charged with treated mineral particles in order to leave hollow spaces in the structure thereof, resulting in a significant reduction in density.

Owing to the fact that said films exhibit improved stability to the stresses they undergo during processing in diaper-production machines, and because, furthermore, they offer an important saving in terms of costs owing to the high mineral-filler content thereof and the low density thereof, they are especially suited to use as an outer covering for disposable diapers and sanitary towels.

7 Claims, 1 Drawing Sheet

COMPOSITION AND PROCEDURE FOR OBTAINING A FILM OF MICRO POROUS THERMOPLASTIC POLYMER THAT IS ESPECIALLY SUITED TO THE PRODUCTION OF PERSONAL HYGIENE ARTICLES SUCH AS DIAPERS AND SANITARY TOWELS

BACKGROUND OF THE INVENTION

On the market there are two different types of outer covering for disposable diapers and sanitary towels, the first type consists of a matt polyethylene film, 18-22 microns thick, the second is obtained by lamination or co-extrusion of a 10-22 micron thick polyethylene film with an unwoven polypropylene fabric to give it a more textile appearance.

Both Types may be breathable or non-breathable.

Breathable films have a water vapour permeable microporous structure that is impermeable to liquid water by capillary pressure. U.S. Pat. No. 6,682,775 by Imerys describes that this structure is obtained by loading a polymer with an important percentage of mineral particles treated superficially with a waterproofing substance that is non adhesive to the base polymer, then extruding the compound as a film by any of the known technologies and subjecting it to single or bi-directional stretching of 1.2-2.5 times in order to increase the size of the pores and join them together.

The non-breathable films are obtained by extrusion and micro embossing of low-density polyethylene, generally linear using titanium dioxide pigments to obtain the desired whiteness and opacity.

Depending on the type of machinery used to make the diapers, and more specifically of the tensions the film is subject to in its passage through this machinery, more or less thickness of the film is necessary to guarantee its dimensional stability. Thus, older machines use films of up to 22 microns and more modern machines use around 18 microns thickness.

Our patent intends to obtain a micro-porous structure with pores of smaller size than in breathable films and not joined to each other, hence not breathable, so a significant reduction of density is achieved at the same time as thanks to the fact that they maintain good mechanical properties at low tensions, they can be manufactured in less thickness, maintaining enhanced dimensional stability in the machines making diapers.

DESCRIPTION OF THE INVENTION

Preparation of the Polymer Compound with the Mineral Load

Selection of the Polymer:

The selected polymer is a polyolefin, for instance and not limited to polyolefins of ethylene, of propylene, or butylene, such as polypropylene, high density polyethylene, medium and low density polyethylene and co-polymers. Low-density polyethylene is preferred and linear low-density polyethylene is more preferably, with a fluidity rate between 1 and 12 (g/10 min at 190° with 2.16 kg) and preferably between 4 and 8. The polymer will be dosed in a mass proportion of 30%-70%, preferably between 40 and 60%.

Selection of the Mineral Load:

The mineral load may be any inorganic compound habitually used in the plastics industry such as for instance (and not limited to) Talc, Kaolin, Calcium or Barium Sulphate, micro-spheres of glass and, preferably Calcium Carbonate.

The size of the particles will subsequently configure the size of the pores and their relative insulation, thus, excessively large particles will tend to produce large-sized pores in open structures, the average size of the particles should be between 0.5 and 4 microns and preferably between 1 and 2 microns to achieve a pore size of 0.2-5 microns.

With the aim of improving dispersion and reducing the adhesion of the particles of the mineral load with the polymer and thus facilitate the formation of the porosity, the particles should have their surface covered with a hydrophobic layer which in addition is incompatible with the polymer used. Any fatty acid commonly used to cover mineral loads such as for instance (and not limited to) stearic, palmitic, oleic, montanic, lauric acids may be used, in a mass proportion of 0.1%-0.5% with regard to the mineral load.

The mineral load will be dosed in a mass proportion of 30%-70%, preferably between 40% and 60%.

Selection of the Adhesive:

The lack of adhesion between the polymer and the particles of the mineral load gives rise to excessively poor mechanical features of the film obtained and, for the same reason, makes control of the size of the micro-pores more difficult, significantly increasing the presence of large-sized pores.

Thus it is necessary to improve the adhesion between the particles of the mineral load and the polymer, for which purpose an adhesive selected from the group comprising co-polymers of the base polymer used with graft polar groups such as for instance (and not limited to) maleic anhydride or acrylic acid. Silane or titanates can also be used.

The adhesive will be dosed in a mass proportion of 1%-5%, preferably between 1.5% and 3%.

In a preferred embodiment, the adhesive consists of a co-polymer of polyethylene with maleic anhydride for a base polymer consisting in a linear low-density polyethylene.

Procedure:

The procedure to obtain the compound film has two stages; a stage of dispersion of the particles of mineral load with the polymer and a film forming stage.

The stage where the mineral loads are dispersed in the polymer may be carried out in a separate operation from known procedures for mixing polymers with loads such as Henschel type powder mixers; Arm mixers of the Brabender type or extruders—double or single worm gear mixers, but it will preferably be carried out directly in the film extrusion line, through a simple or double screw extruder-mixer and more preferably a double screw extruder with a section for removal of gases by means of a vacuum pump with the aim of completely eliminating any moisture introduced by the mineral load that would cause defects on the surface of the film.

This extruder may be connected to the extruders of the film extrusion line by means heated piping so that the molten compound will flow via these pipes to the film extrusion line extruders or directly replace the extrusion line extruders.

The stage where the film is formed will be carried out by technology known as blowing or extrusion of the flat film, taking care so as not to stretch the film cold with the aim of obtaining a pore size from 0.5-5 microns without communication between the pores.

Advantages:

These films provide significant cost savings in comparison to those commonly used for making the outer covering of diapers and sanitary towels, this difference of cost can be specified in the following aspects:

- More dimensional stability to low stretching, allowing a reduction of the film thickness to 14 microns without reducing its stability in diaper manufacturing machines, with up to 20% saving in raw materials.
- Less intrinsic transparency of the film due to the effect of the mineral load, which allows a saving of up to 50% in titanium dioxide.
- Replacement of up to 60% of the polymer by the mineral load with just a 10% increase in density, enabling a saving of up to 30% in raw materials costs.
- The presence of an important percentage of mineral load in the composition of the compound substantially increases its thermal conductivity, enabling an increase of up to 20% in production capacity of the extrusion line.
- At the same time, this mineral load increases surface roughness, improving the efficacy of adhesives used for assembling diaper and sanitary towel parts, while at the same time giving a matt appearance to the film, making the micro-embossing stage of the extrusion line unnecessary.

DESCRIPTION OF THE PREFERRED EMBODIMENT

Embodiment No. 1
Composition:
Dowlex 2035G linear low-density polyethylene: from Dow Chemical, 50%
Mikhart MU 17T calcium carbonate from Provençale: 47%
Amplify GR20 adhesive from Dow Chemical: 3%
Procedure:
The components are mixed in a Buss 6 gk/h extruder, obtaining a compound in the shape of granules of 1.264 g/cm3 density and a fluidity rate of 2.12 g/10 min. with 2.16 kg at 190° C. This compound is fed into a Collin 10 kg/h flat film extruder, producing a single 15-micron layer and stretching it 22% between the extrusion nozzle and the refrigerated cylinder.

A film is obtained with the features detailed in TABLE 1, which is compared with a commercial film commonly used as the outer covering of diapers.
Embodiment No. 1 Presents
  10% more density with 47% less polymer.
  Resistance to deformation by small loads 1.7 times greater, giving it great dimensional stability.
  A moderate loss of resistance to breakage (29%).

TABLE 1

|  | Embodiment Number 1 | Commercial film | Units |
| --- | --- | --- | --- |
| Thickness | 14.1 | 21 | microns |
| Density | 1.04 | 0.95 | g/cm3 |
| Porosity (density reduction) | 18 | 0 | % |
| Surface weight | 14.6 | 19.9 | g/m2 |
| Resistance with 1% elongation | 3.5 | 2 | MPa |
| Resistance with 5% elongation | 6.4 | 5.7 | MPa |

TABLE 1-continued

|  | Embodiment Number 1 | Commercial film | Units |
| --- | --- | --- | --- |
| Resistance with 10% elongation | 7.4 | 8.6 | MPa |
| Resistance to SM breakage | 22.91 | 32.39 | MPa |
| SM breakage elongation | 189.5 | 600 | % |

Figure 1:
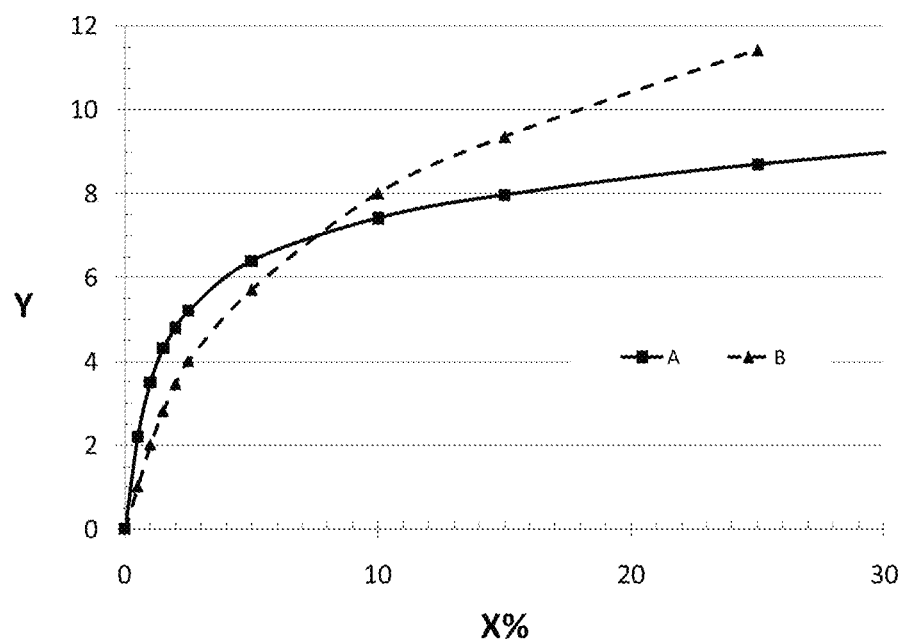
FIG. 1.
Tension-elongation graph obtained according to embodiment no. 1 and from a 21-micron commercial film.
X: Elongation in %
Y: Tension in megapascals
A: Curve of the embodiment no. 1 film
B: Curve of a 21-micron commercial film
Figure 2:
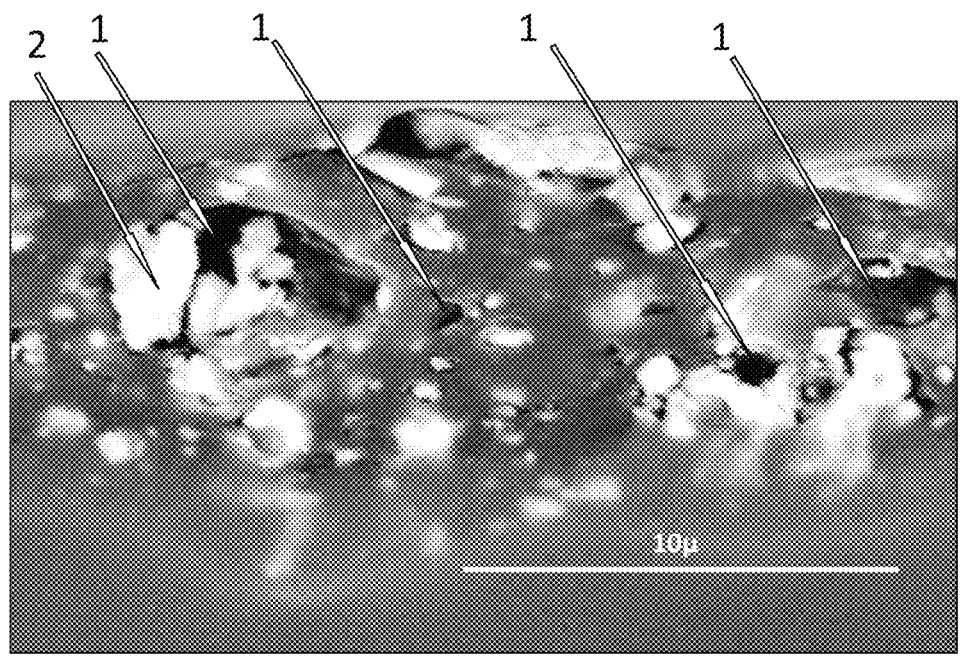
FIG. 2:
Microphotograph of a cross section through the film corresponding to embodiment number 1.
1: micro-pores
2: particles of calcium carbonate

The invention claimed is:

1. A non-breathable film obtained by extrusion comprising a base polymer dosed in a mass proportion between 30% and 70% by weight, loaded with mineral particles dosed in a mass proportion between 70% and 30% by weight covered by a fatty acid in a mass proportion between 0.1% and 0.5% by weight with regard to the mineral particles, and partially adhered to the base polymer by means of an adhesive formed from co-polymers of the base polymer grafted with polar groups comprising maleic anhydride or acrylic add, dosed in a mass proportion between 1% and 5% by weight,
  wherein the average size of the mineral particles is between 0.5 and 4 microns, and wherein said film has a micro-porous structure with a pore size of between 0.2 and 5 microns and the pores are not joined to each other,
  wherein the base polymer is a polyolefin selected from the group consisting of polypropylene, high density polyethylene, medium density polyethylene, and low density polyethylene.

2. The film according to claim 1, wherein the base polymer is a linear low-density polyethylene with a fluidity rate of 1-12 g/10 min and in a mass proportion of 40%-60% by weight.

3. The film according to the claim 1, wherein the mineral particles are selected from the group consisting of talc, kaolin, calcium or barium sulphate, micro-spheres of glass and calcium carbonate.

4. The film according to claim 1, wherein the mineral particles comprise a mass proportion of between 40% and 60% by weight.

5. The film according to dam 1, the mineral particles consist of a stearic acid-coated calcium carbonate, with an average size of the particles between 1 and 2 microns.

6. The film according to claim 1, wherein the adhesive is dosed in a mass proportion of between 1.5% and 3% by weight.

7. The film according to the claim 1, which is a multilayer film.

* * * * *